United States Patent

Shepherd

[11] Patent Number: 6,138,673
[45] Date of Patent: Oct. 31, 2000

[54] INHALATION DEVICE AND METHOD

[75] Inventor: Michael Trevor Shepherd, Quorn, United Kingdom

[73] Assignee: Fisons Limited, Kent, United Kingdom

[21] Appl. No.: 08/995,285

[22] Filed: Dec. 19, 1997

Related U.S. Application Data

[63] Continuation of application No. PCT/GB96/01553, Jun. 28, 1996.

[30] Foreign Application Priority Data

Jun. 29, 1995 [GB] United Kingdom .................... 9513218

[51] Int. Cl.[7] .................................................... A61M 15/00
[52] U.S. Cl. .................................. 128/203.15; 128/203.12
[58] Field of Search ........................ 128/200.22, 203.12, 128/203.15, 203.21, 205.24; 251/74

[56] References Cited

U.S. PATENT DOCUMENTS

| | | | |
|---|---|---|---|
| 390,533 | 10/1888 | Toepfer | 251/74 |
| 933,153 | 9/1909 | Bierly | 251/74 |
| 1,396,394 | 11/1921 | Barrett | 251/74 |
| 3,244,194 | 4/1966 | Henry | 251/74 |
| 4,637,425 | 1/1987 | Petersen | 251/74 |
| 5,141,020 | 8/1992 | Sunderhaus et al. | 137/521 |
| 5,186,164 | 2/1993 | Raghuprasad . | |
| 5,239,992 | 8/1993 | Bougamont et al. . | |
| 5,579,760 | 12/1996 | Kohler . | |
| 5,823,183 | 10/1998 | Casper et al. | 128/203.15 |

FOREIGN PATENT DOCUMENTS

| | | |
|---|---|---|
| 0 347 779 | 12/1989 | European Pat. Off. . |
| 92/04066 | 3/1992 | WIPO . |
| 95/12428 | 5/1995 | WIPO . |
| 96/19253 | 6/1996 | WIPO . |
| 97/31668 | 9/1997 | WIPO . |

Primary Examiner—Aaron J. Lewis
Attorney, Agent, or Firm—Irving Newman

[57] ABSTRACT

An inhalation device comprising a chamber having an inlet and an outlet; and an active substance reservoir, wherein the device further includes vacuum means for forming a vacuum in the chamber and valve means arranged to release the vacuum, so that the substance contained in the reservoir is dispersed in the chamber on release of the vacuum.

16 Claims, 8 Drawing Sheets

INHALATION DEVICE AND METHOD

This Appl is a Continuation of PCT/GB96/01553 filed Jun. 28, 1996.

The present invention relates to an inhalation device and in particular to an inhalation device for helping a user to inhale active substances, particularly anti-asthmatic medicaments in powdered form.

Inhalation devices are known for the administration of medicaments, especially anti-asthmatic medicaments. Inhalation is the preferred route of administration for such medicaments because the dose required to obtain the required anti-asthmatic effect is much lower than when given orally. In addition, some medicaments are poorly absorbed in the gastrointestinal tract.

A number of inhaler devices supply a dispersion of the medicament by means of a gaseous propellant or a pressurised gas such as freon. A disadvantage with such pressurized inhalers is that patients may react adversely to the propellant gases. Further, there is widespread concern about possible environmental damage from freons.

Inhaler devices for administering an active substance in powdered form have also been developed. Devices such as Fisons' Spinhaler (Registered Trade Mark), which is described in UK Patent No. 1,122,284, the TURBUHALER (Registered Trademark) which is described in U.S. Pat. No. 4,524,769, and the device described in European Patent Application 407028, are known to be operated by airflow produced through the device on inhalation by a user. The effectiveness of administration is therefore dependent on a user's ability to inhale strongly and this is undesirable because many users such as children or infirm adults are unable to inhale strongly enough.

WO92/04066 (Bisgaard) discloses an "holding chamber" device comprising a chamber (or spacer) into which active substance may be sucked into a dispersed condition and a mouthpiece by which a patient may inhale dispersed active substance from the chamber. The chamber is defined by at least one wall part which is movable between two positions in which the chamber attains a minimum volume and a maximum volume, respectively, and comprises moving means for biassing the movable wall part towards the position in which the dispersing chamber attains its maximum volume, so as to suck active substance into the dispersing chamber from the reservoir.

In the above device, the wall part is a piston and movement of the piston causes the active substance to be sucked into the dispersion chamber.

The above device suffers from a number of disadvantages. In use, powder will interfere with the seal and the sliding action of the piston, leading to a variability of dose over time. Another disadvantage is that powder dosage is dependent on the amount of travel of the piston which is likely to vary between uses of the device because the spring gets weaker towards the end of the travel of the piston and users will operate the piston to a variable extent. Furthermore, the device is bulky and therefore inconvenient to use.

An object of the present invention is to provide an inhalation device for dispersing active substances which does not require special gaseous propellants and yet can be used by all types of users, even those whose inspired flow rates are low.

According to the invention there is provided an inhalation device comprising a chamber having an inlet and an outlet; and an active substance reservoir; wherein the device further includes vacuum means for forming a vacuum in the chamber and valve means arranged to release the vacuum, so that the substance contained in the reservoir is dispersed in the chamber when the vacuum is released.

Preferably, the inlet is provided with connection means for connecting the chamber to the active substance reservoir so that active substance is drawn into the chamber and dispersed on release of the vacuum. Preferably, the connection means is a housing which permits push-fit connection of the reservoir to the chamber. Conveniently the connection means connect the reservoir to the chamber to form a substantially air-tight seal.

The term "vacuum" is used loosely herein to mean a pressure below atmospheric, typically 700 mbar.

The device of the invention is particularly advantageous because the valve means provide for quick release of the vacuum. This feature is particularly advantageous because the rapid influx of air into the chamber achieves a very effective dispersion of the respirable form of the active substance in the chamber. The device of the invention can produce a 70% powder dispersion instead of the 30% dispersion normally achieved with conventional devices. The effective powder dispersion afforded by the device of the invention produces an increased amount of easily inspired fine powder particles compared to known devices.

Preferably the valve means comprises a hinged flap which is movable from a sealed condition in which it seals the inlet to a released condition in which active substance can be drawn into the chamber. Alternatively, the hinged flap may be provided on a second chamber inlet, comprising a bored plug for example.

Preferably, the hinged flap is held in the sealed condition by a releasable catch.

Preferably, the hinged flap is biassed into the released condition, conveniently by means of a spring. Alternatively, the flap is pushed adequately open by the rush of air and held by a retaining means, and then released for return to the sealing position.

Preferably, the active substance is a medicament in the form of a powder and the reservoir is conveniently adapted to dispense a metered dose of powder. The medicament may consist solely of an active ingredient, for example a hygroscopic drug. Active ingredients which may be mentioned include sodium cromoglycate, nedocromil sodium, salbutamol and terbutaline. We prefer the medicament to additionally comprise an inert carrier, especially in the case of tightly compacted bodies of medicament, because this results in improved dispersion characteristics. Suitable inert carriers include sugars, for example lactose. When an inert carrier is present we prefer the particle size of the carrier to be larger than that of the active ingredient. Suitable particle sizes for the active ingredient when in loose powder form are from 1 to 10 $\mu$m.

Formulations of the medicament which may be mentioned include a mixture of any one of the above-mentioned active ingredients in association with lactose, the proportions of carrier to active ingredient being dependent upon the particular substances present. For example, we have found that a 1:1 mixture of nedocromil sodium or sodium cromoglycate with lactose is advantageous.

Advantageously, the reservoir comprises a dry powder inhaler.

Preferably, the vacuum means comprises first and second parts of the chamber sealingly connected together and movable relative to one another to increase the volume of the space defined within the chamber and thereby create a vacuum.

Preferably, screw thread means are provided on the chamber parts whereby the space defined within the chamber is increased by rotating one part relative to the other part. Typically, the desired vacuum is achieved in two complete turns (720°) or less. A ratchet or similar means may be provided to prevent the vacuum reversing the action in between turns, with there being a quick release mechanism to allow the user to return the device to the starting position.

Preferably, the screw thread is arranged as a multi-start thread which both spreads the load and makes it easier for a user to re-assemble the device after it has been dismantled for cleaning.

Preferably, the hinged flap is connected to the connection means and the connection means is rotatable whereby rotation of the connection means disengages the releasable catch and permits the hinged flap to move to the released condition. Alternatively, a pivoted latch mechanism is moved away from the edge of the hinged flap to release it.

Preferably, the releasable catch comprises tang means arranged in the chamber and engageable with a portion of the hinged flap in the sealed condition.

In a further aspect the invention provides a method of dispersing an active substance for inhalation, the method comprising:

providing an active substance reservoir and a chamber having an inlet and an outlet;

forming a vacuum in the chamber; and operating valve means to release the vacuum so that the active substance contained in the reservoir is dispersed in the chamber on release of the vacuum.

Preferably, the method comprises connecting the chamber to the active substance reservoir so that the active substance contained in the reservoir is drawn into the chamber and dispersed on release of the vacuum.

After a user has effected dispersion of the active substance by operating the device he can inhale the dispersed substance through the outlet of the chamber, which outlet is preferably formed as a mouthpiece, with a facemask if necessary, provided with a one-way valve. The one-way valve prevents moist exhaled air from entering the chamber of the device, which could be a problem if the active substance is in powdered form, and also prevents the desired dose from being blown out of the device.

Conveniently, the outlet of the device is held to a users' mouth before the vacuum is released because movement of the chamber after firing may cause the aerosol of powder to hit the chamber walls and thereby reduce the amount of active substance which can be inhaled.

Preferred embodiments of the invention will now be described, by way of example only, with reference to the accompanying drawings in which.

As shown, a preferred inhalation device of the invention comprises a two-part cylindrical chamber 1 having an inlet 2 and an outlet 3. Preferably, the chamber parts are made from a material comprising polypropylene and styrene-ethylene butalene-styrene (SBS), known under the tradename Evoprene.

The parts of the cylinder are sealed together by an internal rubber seal 1a, as shown.

Figure 9:
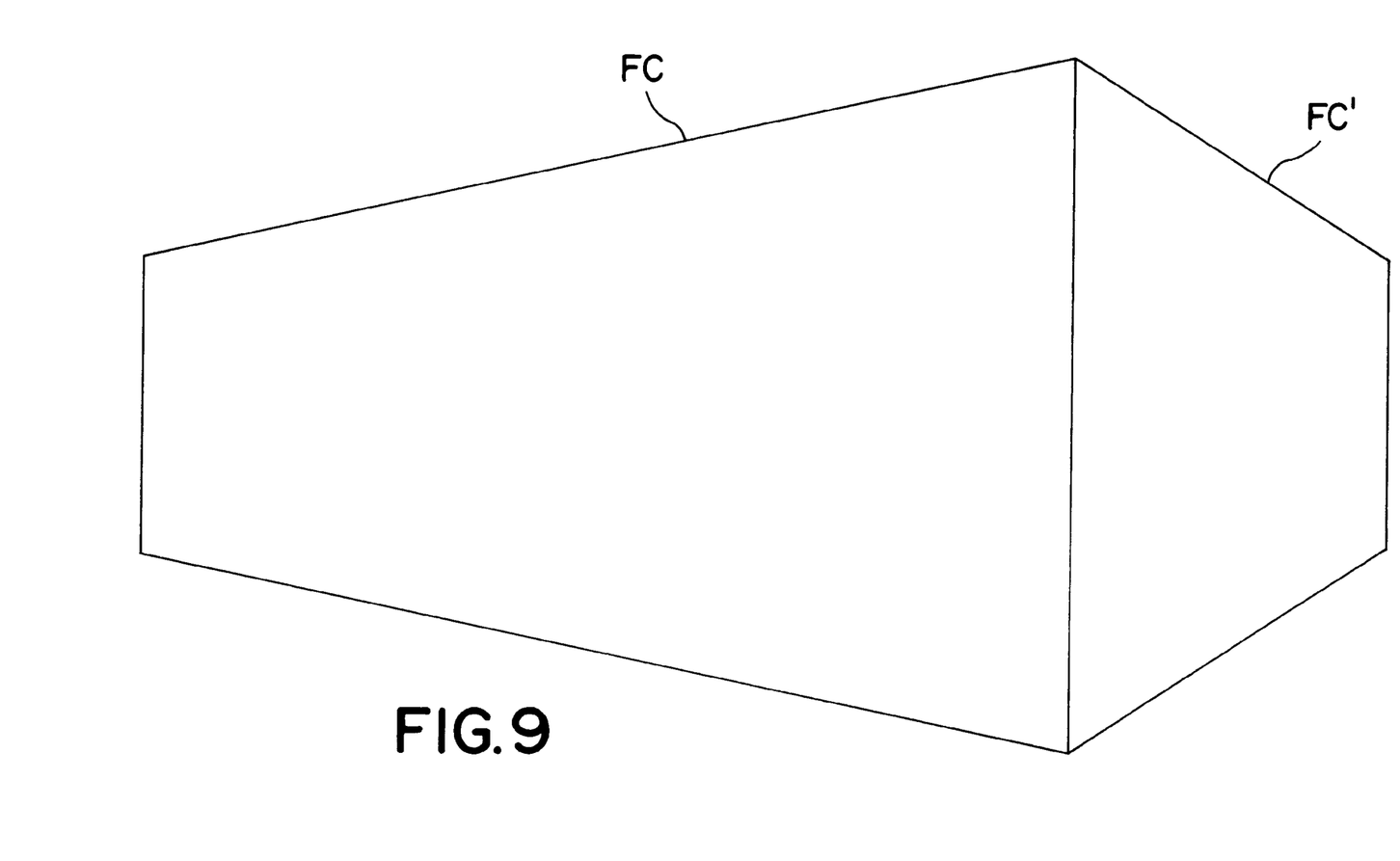
FIG. 9 shows the chamber shape of a further embodiment of the invention.

Whilst the chamber 1 is shown as a cylinder in FIGS. 1 to 7, it will be appreciated that other chamber shapes can be used. Another preferred chamber shape is shown in FIG. 9. As shown, the chamber comprises coaxial, opposing frustoconical parts FC and FC' which are sealingly connectable at their bases.

The inlet 2 is provided as a housing 4 with connection means 5 into which MDPI 6 is a push-fit.

The housing 4 and connection means can be especially designed for a particular MDPI or can be made of deformable material to suit different MDPIs.

Figure 5A:
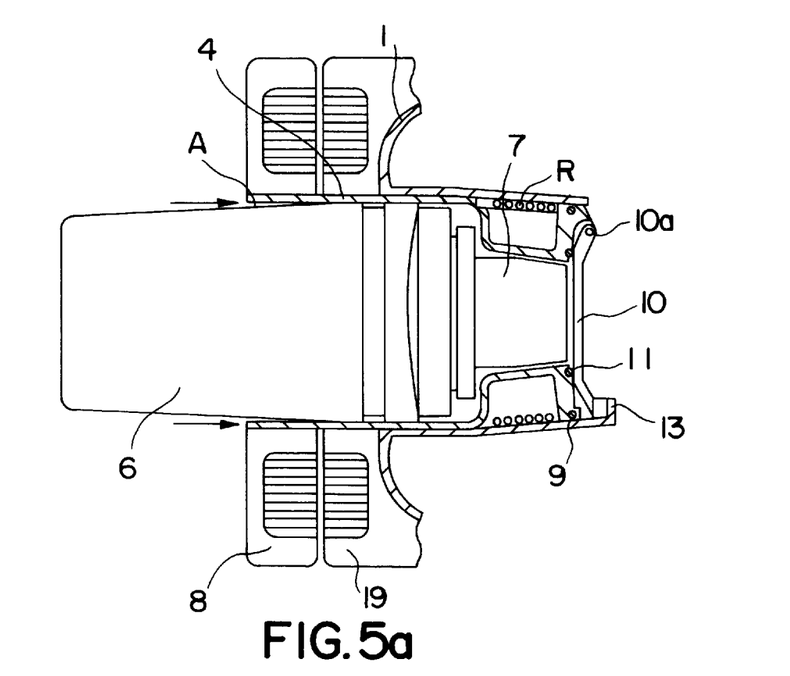
FIGS. 5a, 5b and 5c are sections through a device of the invention in a sealed condition.

An air pathway A is provided between the MDPI and the housing by means of internal grooves in the housing, as shown in FIG. 5a. The grooves are so dimensioned as not to provide any significant restriction to flow beyond that provided by the rest of the device.

The mouthpiece 7 of the MDPI is a close-fit, and preferably an air-tight seal against the housing 4.

Figure 1:
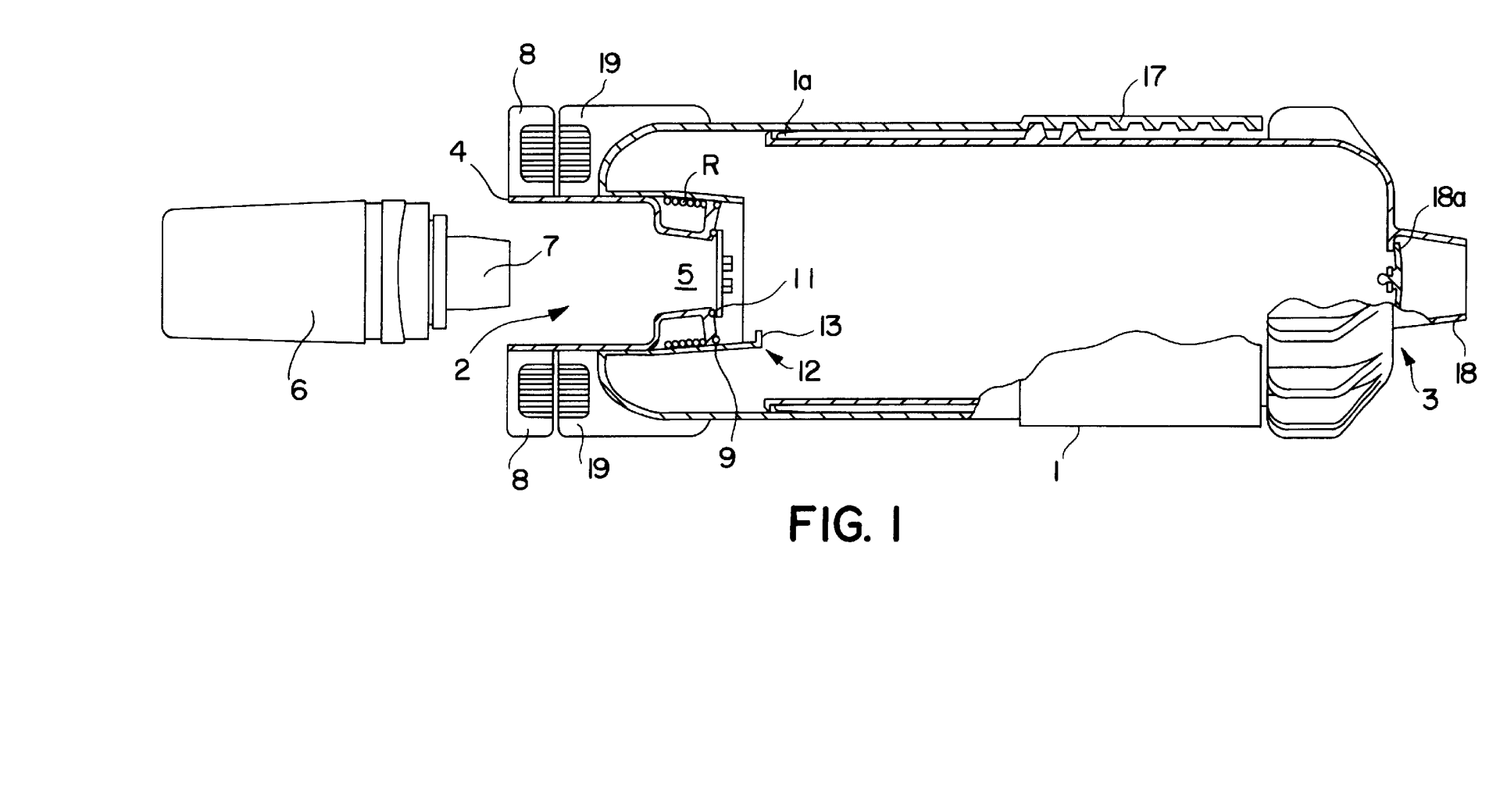
FIG. 1 is a partial section through a device of the invention for connection with a metered dose powder inhaler (MDPI)
Figure 2A:
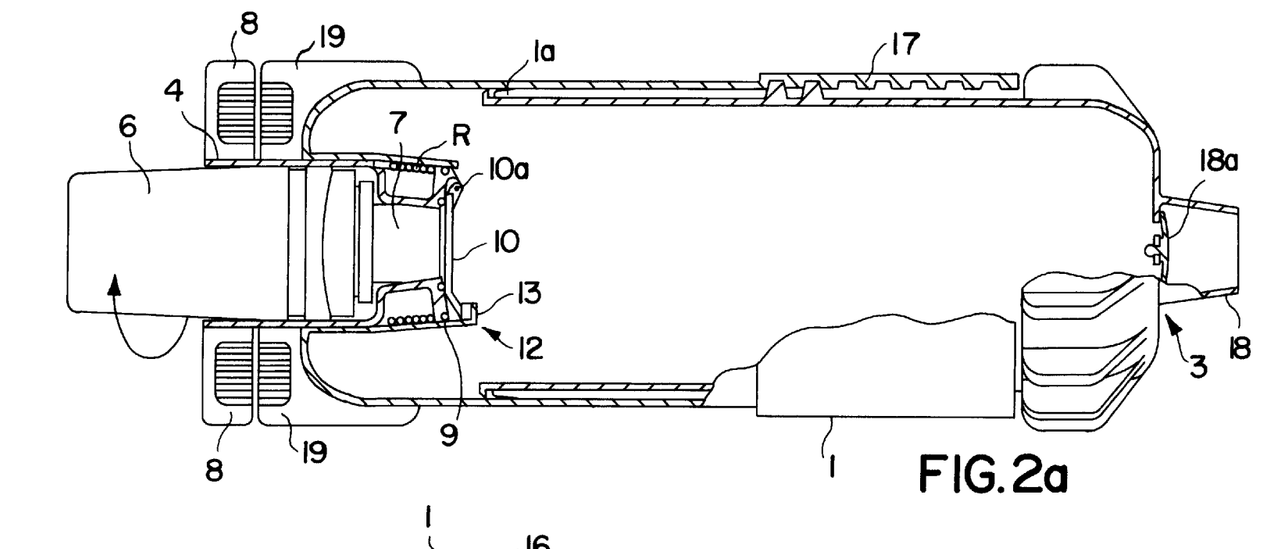
FIGS. 2a and 2b show the device of FIGS. 5a to 5c.
Figure 2B:
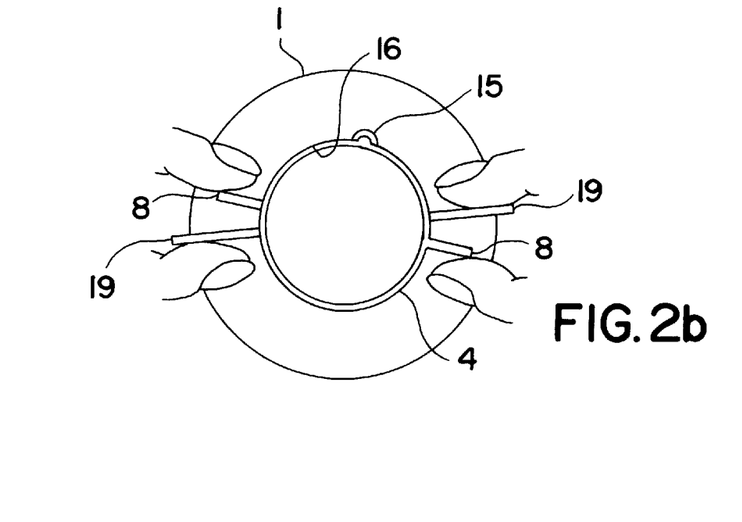
Figure 6A:
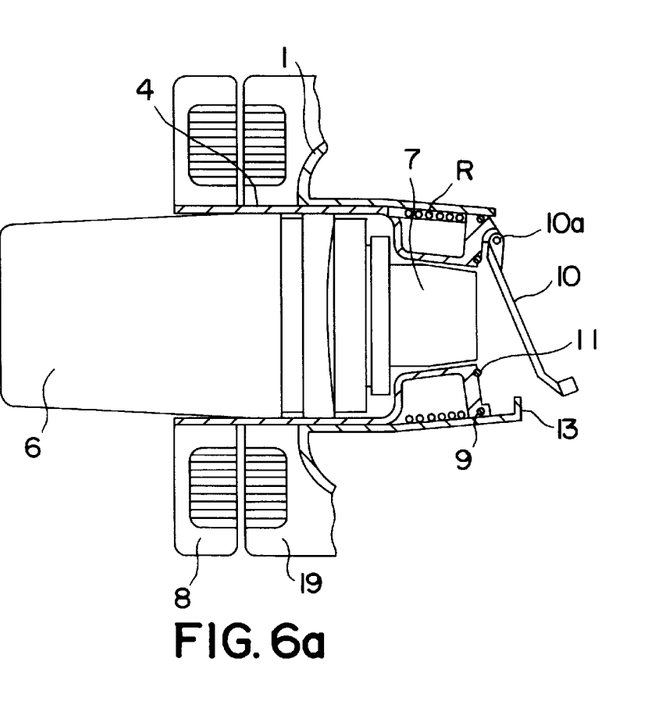
FIGS. 6a, 6b and 6c are sections through the device of FIGS. 5, 5b and 5c in a released condition.

The housing 4 is preferably located in a cylindrical recess within the chamber, as shown in FIGS. 1 and 5a and 6a.

The housing 4 and connected MDPI 6 can be rotated uni-directionally relative to the chamber by means of the finger grips 8. Rotation in the opposite direction is prevented by a coil spring ratchet R which expands to lock onto the bore of the chamber 1.

An 'O' ring 9 provides a vacuum seal between the housing 4 and chamber 1. However, other seal means such as two-part engageable moulding arrangement could replace the "O" ring, if desired.

Figure 5B:
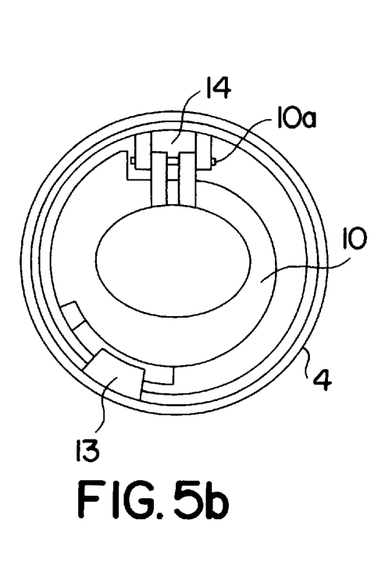
Figure 5C:
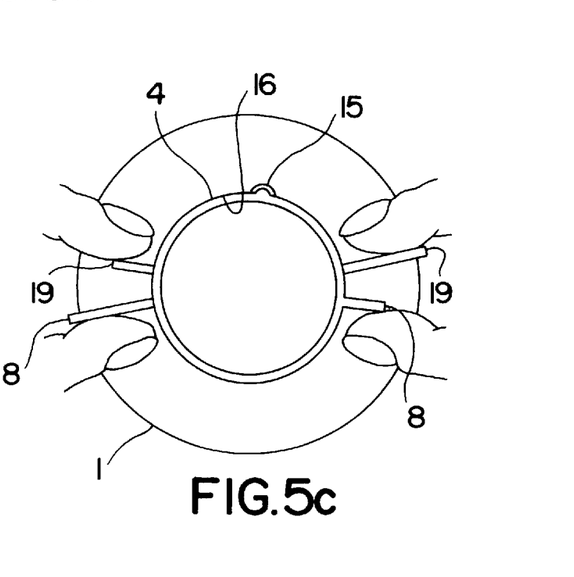
Figure 6B:
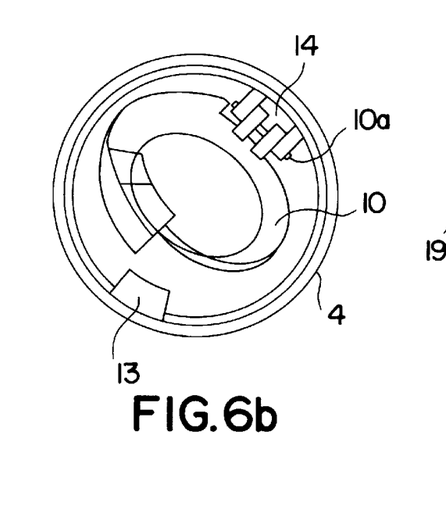
Figure 6C:
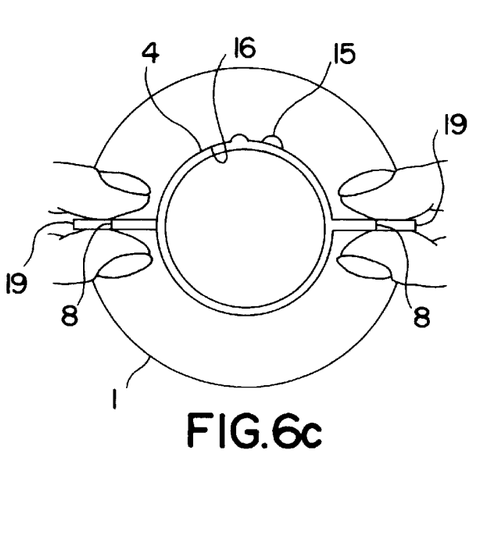

As shown in FIGS. 5b and 6b, a flap 10 is hinged 10a to the housing 4 and can be held closed tight against the rubber flap seal 11 by means of a releasable catch 12 in the form of a tang 13 provided on the chamber 1

As shown in FIGS. 5a and 6b, the flap 10 is asymmetrical so that when the tang 13 lies to one side of the flap (FIG. 5b) the flap is held in the closed condition. However, when the housing is progressively rotated the tang suddenly loses engagement with the flap (FIG. 6b). The flap is then immediately urged into the released or open condition by the vacuum differential pressure, preferably with the assistance of biassing means such as a spring 14.

Further rotation of the housing (after firing or discharge) causes the tang 13 to re-engage and reclose the flap 10 into the sealed condition in preparation for re-use.

In use, the MDPI 6 is first set to dispense a metered dose of powder and inserted into the housing 4. The finger grips 8 are then rotated to close the flap 10 in the sealed condition, and to bring the tang 13 to the point of firing. This position is indicated to the user by the detent feature 15 shown in FIGS. 2b, 4b, 5c and 6c, arranged between the housing 4 and the bore 16 of the chamber 1.

The detent feature is advantageous because a click can be felt/heard by the user as the above position is attained.

Figure 3:
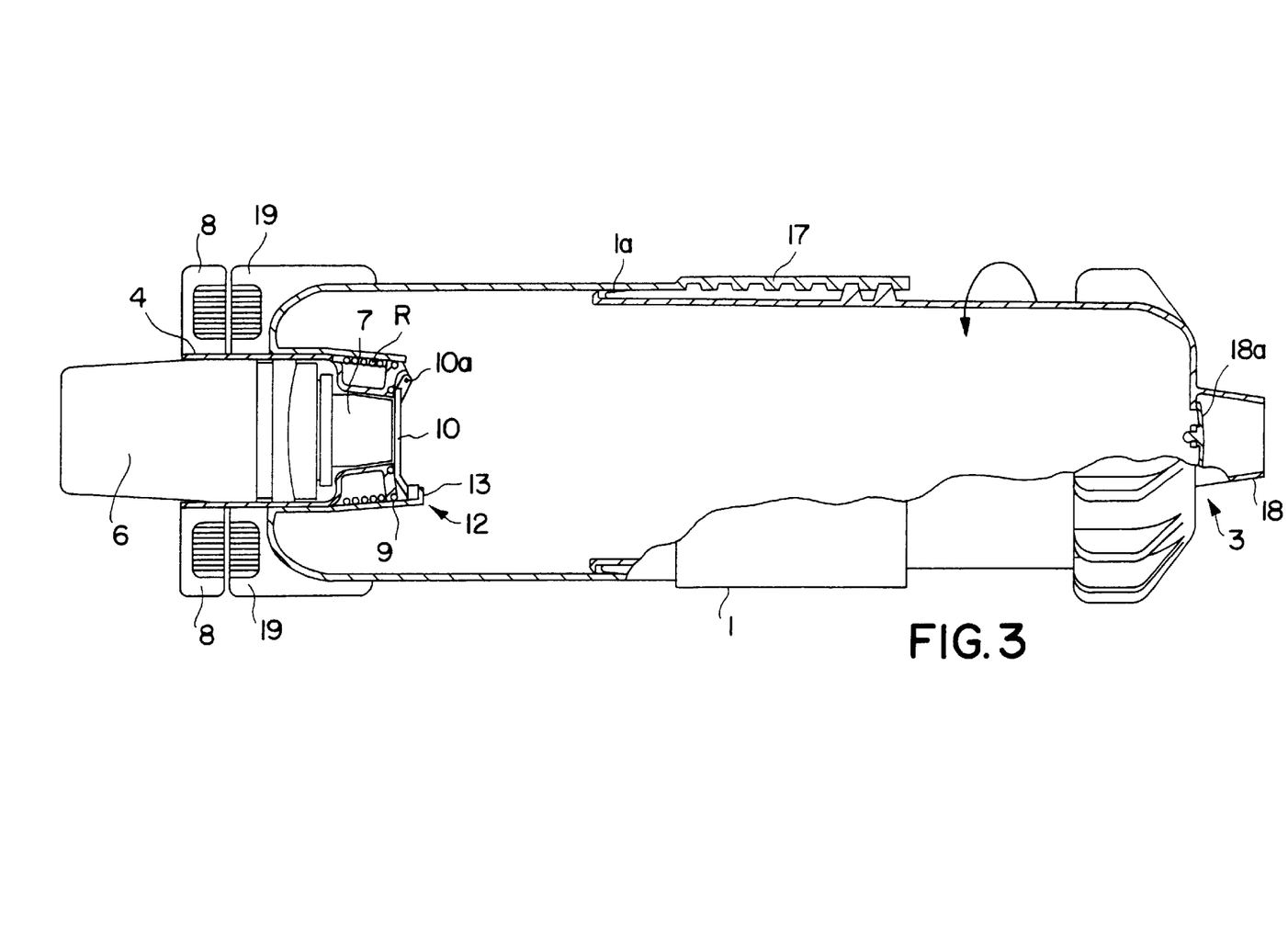
FIG. 3 is a partial section through the device of FIGS. 2a and 2b showing rotation of the housing relative to the chamber to generate a vacuum.

In the embodiment shown, a vacuum is generated by rotating the parts of the chamber 1 relative to one another to operate the helix of the screw thread 17, as shown in FIG. 3. Preferably, the volume of the chamber is increased from an initial 550 ml at atmospheric pressure to 750 ml at vacuum.

A volume of 750 ml is convenient because such a volume can be inhaled easily by a child, so the device can readily supply one dose of active ingredient per lungful inhaled from the chamber.

The coarse three-start thread shown gives a 52 mm elongation over a two-revolution twist of the two chamber parts.

Figure 4A:
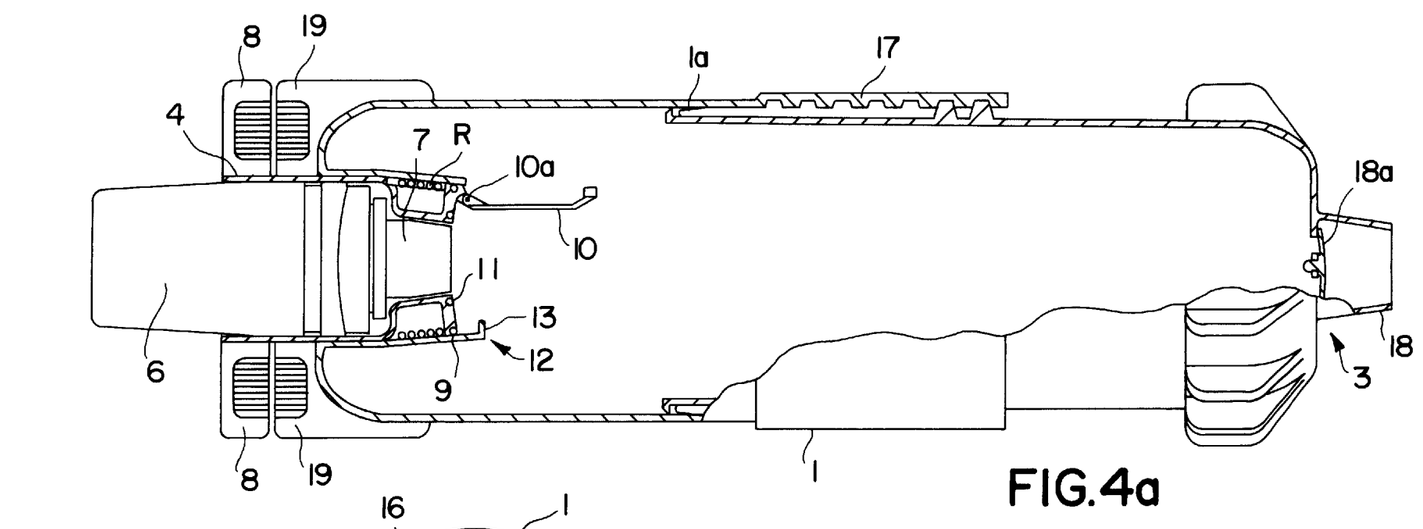
FIGS. 4a and 4b are sections showing the pressure release, or firing of the MDPI to disperse the active substance in powdered form in the chamber.
Figure 4B:
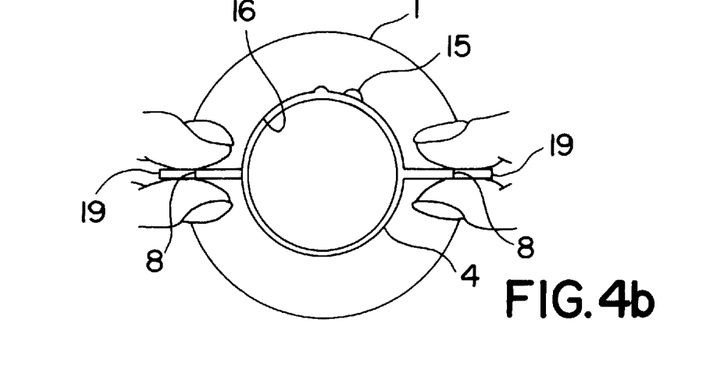

To fire the device, the mouthpiece 18 at the outlet of the inhalation device is held to the mouth and a squeezing action applied between the finger grips 8 and the chamber ribs 19, as shown in FIG. 4b.

This releases the detent means and the tang 13 loses engagement with the flap 10. The flap is then immediately urged into the released condition by the vacuum differential pressure, preferably with the assistance of the biassing spring 14.

A dose of powder is dispersed effectively in the chamber by the rapid influx of air to form an aerosol cloud that can be inhaled easily by a user. As inhalation proceeds, fresh air is drawn into the inlet 2 of the chamber 1 through the MDPI 6. In the device shown no separate inlet valve is included to allow auxiliary input of air into the chamber, but such an inlet could be provided if desired. If such an inlet valve is included it is arranged to be opened shortly after the device fires.

The mouthpiece 18 is provided with a conventional rubber or polymeric flap valve 18a to prevent any moist exhaled air from entering the chamber 1, and to keep the vacuum until released.

Although the single-stroke screw threaded vacuum means 17 described above is particularly preferred, a skilled reader will appreciate that the generation of a vacuum in the chamber before firing can be achieved by a variety of other vacuum means.

Figure 7:
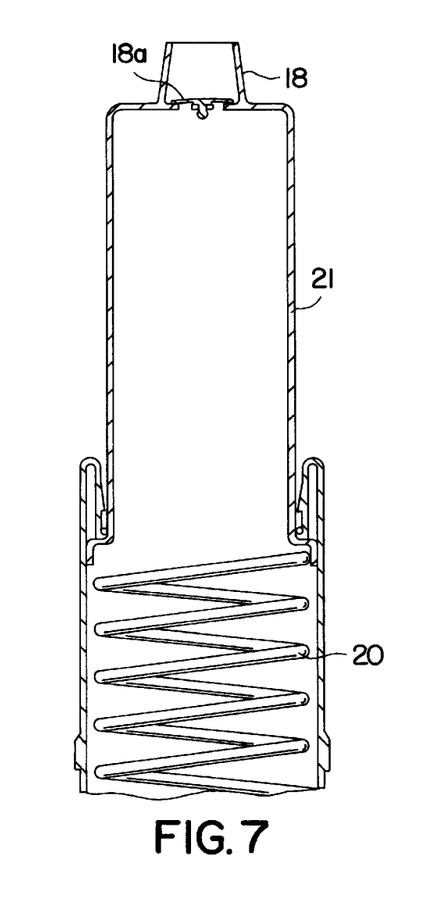
FIG. 7 shows an alternative vacuum means comprising a plunger and spring arrangement.

An alternative vacuum means comprising a single-stroke spring 20 and plunger (or piston) 21 arrangement in the chamber is shown in FIG. 7.

In this embodiment, the plunger 21 is pushed against the spring 20 and its release generates a vacuum. A vacuum release such as a releasable catch (not shown) opens the flap valve to allow an active substance to be dispersed into the chamber from the reservoir.

Figure 8A:
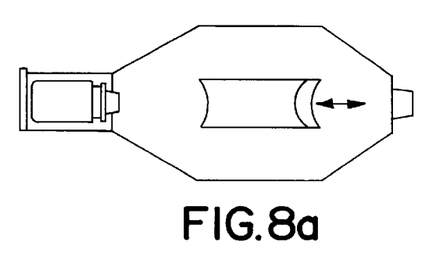
FIGS. 8a and 8b show vacuum means of further embodiments comprising a finger or hand-operated vacuum pump arrangement.
Figure 8B:
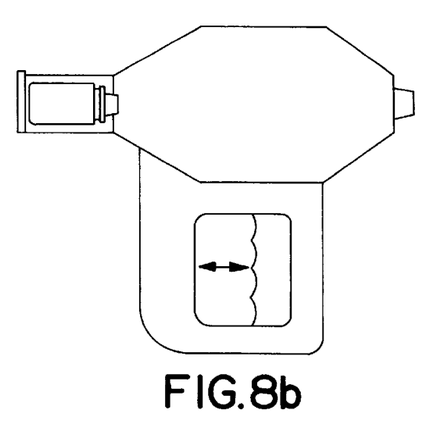

In another embodiment the vacuum is generated by multi-stroke pump arrangements, as shown in FIGS. 8a and 8b, including a separate hand or finger operated vacuum pump provided with inlet and outlet valves to the chamber.

However, the latter two vacuum means are less convenient because they are difficult to dismantle and clean and/or relatively bulky compared to the preferred screw threaded vacuum means.

Experiments

The preferred device was tested using a known MDPI Fisons' ULTRAHALER™, described in EP 0,407,028 A2. The effectiveness of the device of the invention as an aid to the inhalation of a powdered medicament (Fisons' Tilade™) was tested in a known manner by using a multi-stage liquid impactor like the Astra-Copley impactor. The test device comprises a model respiratory tract and lung arrangement and enables one to determine the amount and size of particles which would reach various locations in the human body.

The results are presented in Tables 1 and 2. The key results relate to the weight of medicament reaching the locations S3, S4 and filter, as these locations indicate the respirable fraction administered to the user, that is, amount of medicament of a size which can be respired to confer the desired therapeutical effect in the lower lungs.

TABLE 1

Cylindrical chamber

| Location | mg/Dose at Location | |
|---|---|---|
| Upper Duct | 0.057 | Total Weight Recovered per Dose (mg) 1.877 |
| Lower Duct | 0.022 | Total Weight in Cloud per Dose (mg) 1.733 (92.33%) |
| Mouthpiece | 0.065 | |
| Throat | 0.159 | |
| S1 | 0.121 | Total Weight in 3, 4 and Filter per Dose (mg) 1.307 (69.63%) |
| S2 | 0.146 | |
| S3 | 0.371 | |
| S4 | 0.826 | Mean Shot Weight (mg) 12.6 |
| Filter | 0.110 | |

TABLE 2

Chamber shape as shown in FIG. 9

| Location | mg/Dose at Location | |
|---|---|---|
| Upper Duct | 0.024 | Total Weight Recovered per Dose (mg) 1.309 |
| Lower Duct | 0.036 | Total Weight in Cloud per Dose (mg) 1.208 (92.28%) |
| Mouthpiece | 0.041 | |
| Throat | 0.068 | |
| S1 | 0.040 | Total Weight in 3, 4 and Filter per Dose (mg) 1.010 (77.16%) |
| S2 | 0.090 | |
| S3 | 0.285 | |
| S4 | 0.692 | Mean Shot Weight (mg) 11.5 |
| Filter | 0.033 | |

The results show that over 90% of the powder dose is inhaled from the chamber and reaches the users' throat, and that approximately 70% to 80% of this material is of a size that can reach the lower lungs as desired.

The coaxial, opposing frustoconical chamber parts shown in FIG. 9 were particularly effective. This may be because this chamber shape is more suited to the shape of the cloud of dispersed powder produced when the vacuum is released, that is, the respirable fraction of the powder cloud does not impact the walls of the chamber as much as it does with the cylindrical chamber. This would allow more of the respirable fraction of the powder cloud to be inhaled from the chamber compared to the cylindrical chamber.

The effectiveness of the device of the invention in administering medicaments, particularly in powdered form, to the location in the body of user where the therapeutic effect is required means that a user is less likely to suffer from possible adverse side-effects of the medicaments. This makes the device particularly suitable as an inhalation aid for steroidal medicaments which are known to produce adverse side-effects.

What is claimed is:

1. An inhalation device comprising a chamber having an inlet and an outlet; an active substance reservoir; a vacuum means for forming a vacuum in the chamber, a valve means which is operable to release the vacuum; and a connection means for connecting the chamber to the active substance reservoir; wherein the active substance is in the form of a dry powder and is administered as a dry powder, the reservoir is adapted to dispense a metered dose of the powder; and the substance contained in the reservoir is drawn into and dispersed in the chamber on release of the vacuum.

2. A device as claimed in claim 1 wherein the valve means comprises a hinged flap which is movable from a sealed condition, in which it seals the inlet, to a released condition.

3. A device as claimed in claim 1 wherein the reservoir comprises a dry powder inhaler.

4. A device as claimed in claim 1 wherein the connection means comprise a push-fit connection means.

5. A device as claimed in claim 1 wherein the connection means connect the reservoir to the chamber to form a substantially air-tight seal.

6. The device as claimed in claim 1 wherein the vacuum means comprises a single stroke spring and plunger arrangement.

7. The device as claimed in claim 1 wherein the vacuum means comprises a multi-stroke pump.

8. A method of dispersing an active substance for inhalation, the method comprising:

providing an active substance reservoir, adapted to dispense a metered dose of dry powder;

providing a chamber having an inlet and an outlet;

connecting the chamber to the active substance reservoir;

forming a vacuum in the chamber; and operating valve means to release the vacuum so that the active substance contained in the reservoir is dispersed in the chamber on release of the vacuum.

9. A method as claimed in claim 8 wherein the active substance is a hygroscopic medicament.

10. A method as claimed in claim 9 wherein the hygroscopic medicament is selected from sodium cromoglycate, nedocromil sodium, salbutamol and terbutaline.

11. An inhalation device comprising a chamber having an inlet and an outlet; an active substance reservoir; a vacuum means for forming a vacuum in the chamber, a valve means which is operable to release the vacuum; and a connection means for connecting the chamber to the active substance reservoir; wherein the active substance is in the form of a dry powder and is administered as a dry powder, the reservoir is adapted to dispense a metered dose of the powder; and the substance contained in the reservoir is drawn into and dispersed in the chamber on release of the vacuum, wherein said valve means comprises a hinged flap which is movable from a sealed condition, in which it seals the outlet, to a released condition, and the hinged flap is held in the sealed condition by a releasable catch.

12. A device as claimed in claim 11 wherein the hinged flap is biassed into the released condition.

13. A device as claimed in claim 11, wherein the releasable catch comprises a tang means arranged in the chamber and engageable with a portion of the hinged flap in the sealed condition.

14. A device as claimed in claim 13 wherein the hinged flap is connected to the connection means and the connection means is rotatable, whereby rotation of the connection means disengages the releasable catch and permits the hinged flap to move to the released condition.

15. An inhalation device comprising a chamber having an inlet and an outlet; an active substance reservoir; a vacuum means for forming a vacuum in the chamber, a valve means which is operable to release the vacuum; and a connection means for connecting the chamber to the active substance reservoir; wherein the active substance is in the form of a dry powder and is administered as a dry powder, the reservoir is adapted to dispense a metered dose of the powder; and the substance contained in the reservoir is drawn into and dispersed in the chamber on release of the vacuum, wherein the vacuum means comprises parts of the chamber sealingly connected together and movable relative to one another to increase the volume of the space defined within the chamber and thereby create a vacuum.

16. A device as claimed in claim 15 wherein thread means are provided on the chamber parts whereby the space defined within the chamber is increased by rotating the parts relative to one another.

* * * * *